(12) United States Patent
Engvall

(10) Patent No.: US 8,048,045 B2
(45) Date of Patent: Nov. 1, 2011

(54) BLOOD LEAKAGE DETECTION DEVICE

(75) Inventor: Daniel Engvall, Halmstad (SE)

(73) Assignee: Redsense Medical Malta Ltd, Msida (MT)

( * ) Notice: Subject to any disclaimer, the term of this patent is extended or adjusted under 35 U.S.C. 154(b) by 230 days.

(21) Appl. No.: 11/869,039

(22) Filed: Oct. 9, 2007

(65) Prior Publication Data

US 2008/0249487 A1    Oct. 9, 2008

(30) Foreign Application Priority Data

Apr. 4, 2007  (SE) ...................................... 0700845

(51) Int. Cl.
*A61F 13/02* (2006.01)
*A61H 33/04* (2006.01)
*A61H 13/00* (2006.01)

(52) U.S. Cl. .......................... 604/307; 604/308; 604/304

(58) Field of Classification Search .................. 604/304, 604/307, 308
See application file for complete search history.

(56) References Cited

U.S. PATENT DOCUMENTS

| | | | | |
|---|---|---|---|---|
| 3,299,890 | A | * | 1/1967 | Parker ............................. 602/77 |
| 5,201,755 | A | * | 4/1993 | Klement ........................ 606/194 |
| 5,557,263 | A | * | 9/1996 | Fisher et al. ................... 340/605 |
| 5,579,765 | A | | 12/1996 | Cox et al. |
| 5,779,657 | A | | 7/1998 | Daneshvar |
| 2002/0137999 | A1 | | 9/2002 | Bandeian et al. |
| 2002/0198483 | A1 | | 12/2002 | Wariar et al. |
| 2004/0225255 | A1 | * | 11/2004 | Ono ................................ 604/65 |
| 2005/0038325 | A1 | | 2/2005 | Moll |

FOREIGN PATENT DOCUMENTS

| | | |
|---|---|---|
| EP | 1 472 973 A1 | 11/2004 |
| WO | WO-9924145 A1 | 5/1999 |
| WO | WO-2006/001759 A1 | 1/2006 |

* cited by examiner

*Primary Examiner* — Michele M Kidwell
(74) *Attorney, Agent, or Firm* — Dickstein Shapiro LLP

(57) ABSTRACT

A blood leakage detection device for attachment to the skin of a patient at a wound such as one caused by insertion a cannula into a vein or artery comprises a support of a flexible material having a top side and an opposite bottom side, a zone of adhesive for attachment to the skin on the bottom side of the support extending along its periphery except for a sector of from about 5° to about 150°, a blood absorbent patch disposed on the support and extending inwardly of the adhesive zone and, optionally, in the sector, and a blood detection probe comprising a probe head disposed at or near the center of the support in the absorbent patch or abutting the bottom side thereof. A blood transport element can be disposed between the support and the absorbent patch.

19 Claims, 7 Drawing Sheets

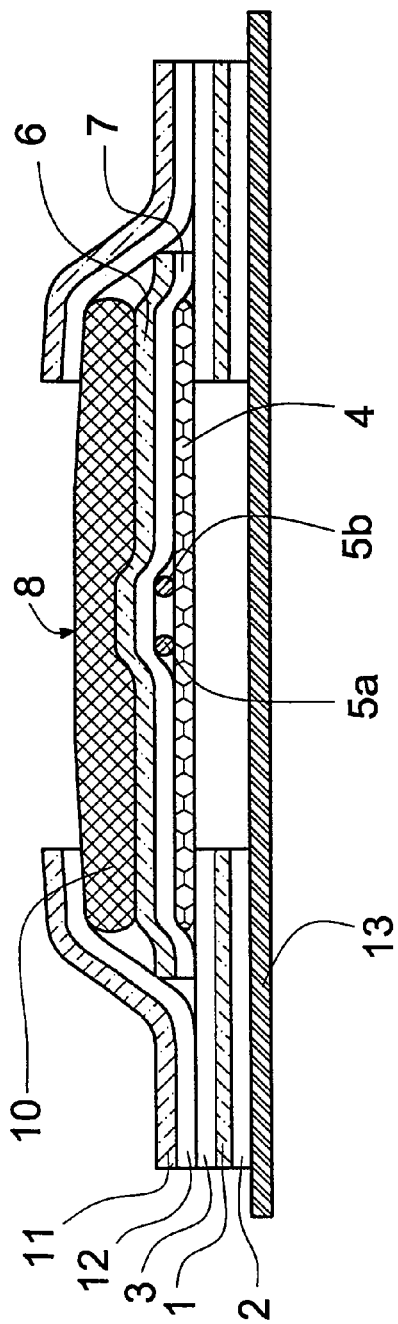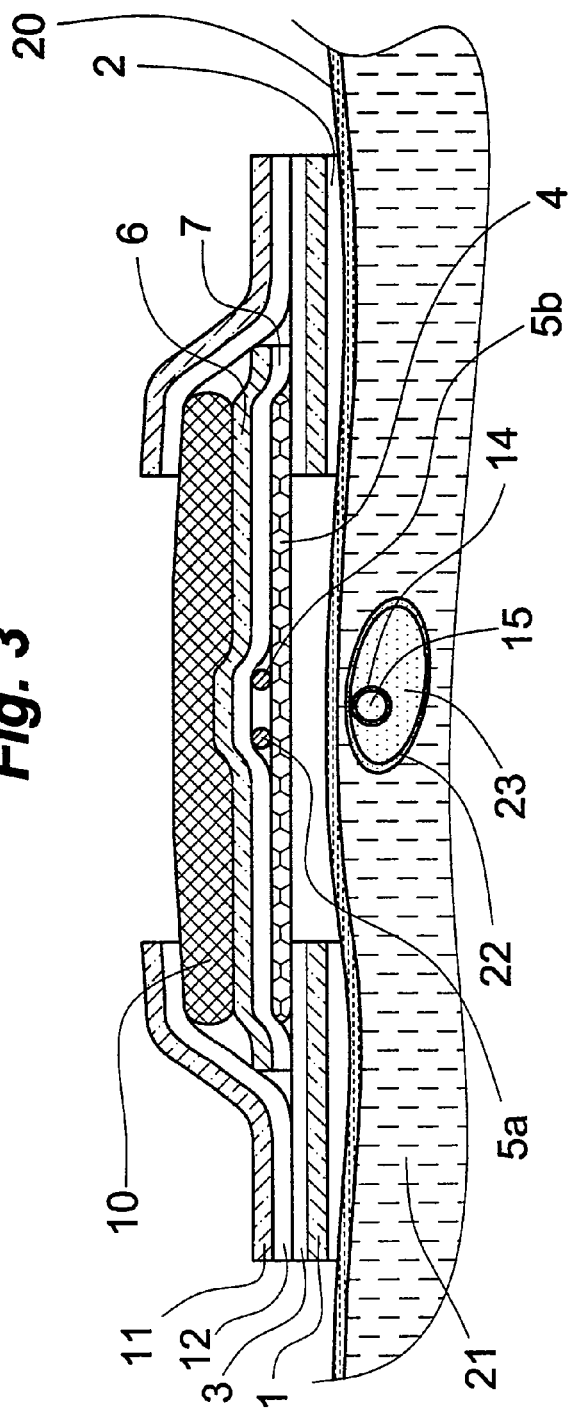

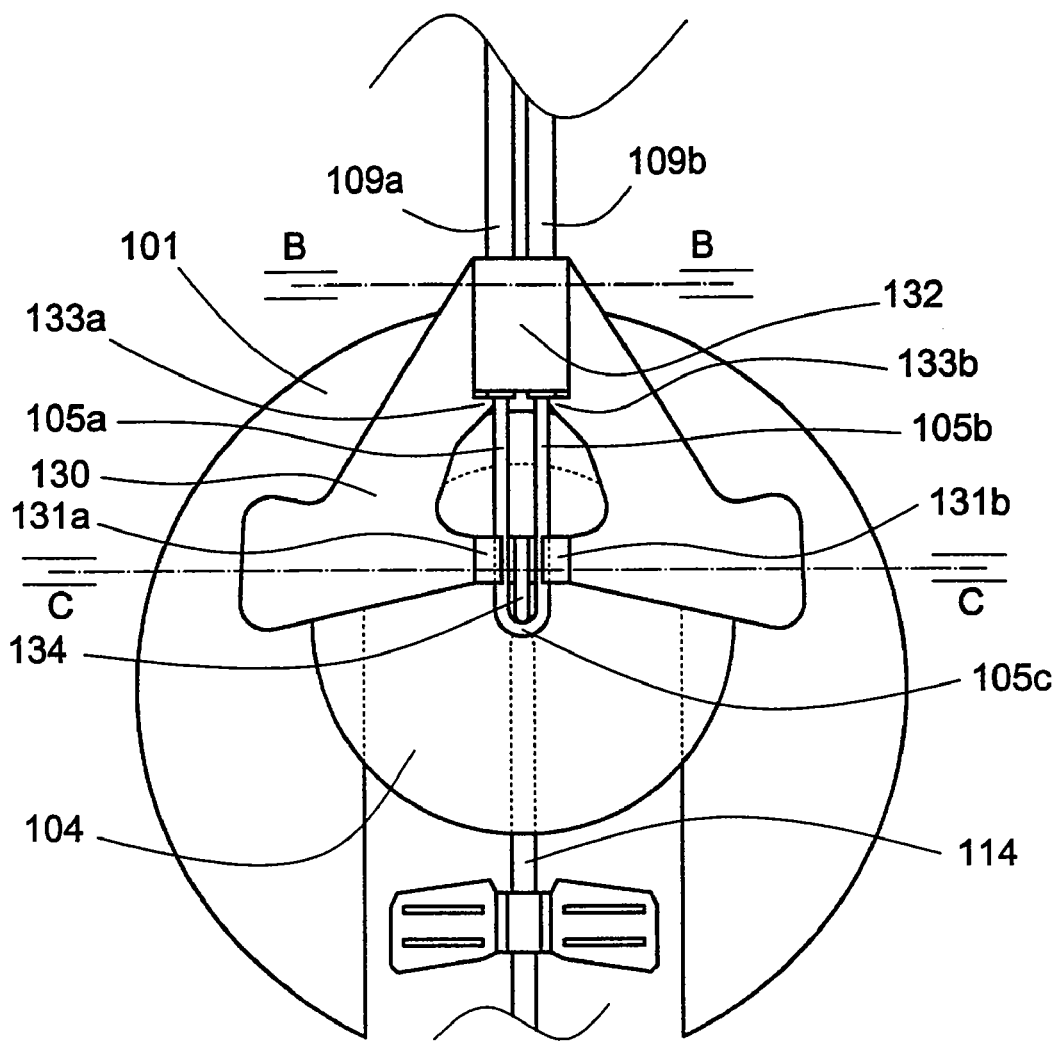
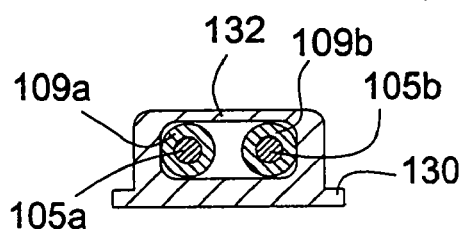
Fig. 5
Fig. 5a
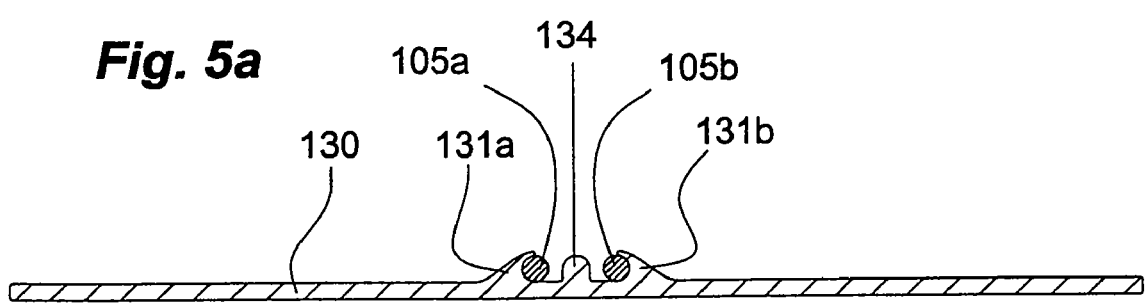
Fig. 5b

BLOOD LEAKAGE DETECTION DEVICE

FIELD OF THE INVENTION

The present invention relates to a device for use in detecting blood leakage from a wound by optical or electrical means, in particular a wound caused by insertion of a cannula into a vein or artery, or a cannula or fistula catheter into an arteriovenous fistula or graft.

BACKGROUND OF THE INVENTION

In blood dialysis wounds are caused by puncturing an artery or vein by a cannula or an arteriovenous (AV) fistula or graft by a cannula or fistula catheter to remove blood for dialysis. The purified blood is returned to the patient by venous infusion through a second cannula or fistula catheter. A cannula or fistula catheter of this kind is usually secured to the patient's skin by adhesive tape. During dialysis the cannula or fistula catheter may be accidentally withdrawn. This results in immediate bleeding which, if is not noticed and stopped at once, may lead to the loss of a large volume of blood. Also other wounds that have been closed by surgery or by mere coagulation may start to bleed again, for instance during sleep, and thereby put the patient at risk if the bleeding is not noticed and stopped with in a short time.

An apparatus for detection of blood leakage from wounds is disclosed in WO 2006/001759 A1. The known apparatus comprises a single use disposable blood leakage detection device comprising a patch, a means for temporary fixation of the patch at a wound, an optical fibre for conducting light from electronic emission means to electronic detection means of the apparatus, the fibre at its passage via the patch comprising a zone in which the reflectance of the fibre wall in respect of the light conducted by the fibre is affected by blood conducting the wall in the zone, a difference in returned light indicating a leakage of blood from the wound. At its free ends the fibre comprises connectors to put it in radiative communication with the emission and detection means.

OBJECTS OF THE INVENTION

One object of the present invention is to provide an improved blood leakage detection device for use with apparatus for optical or electrical detection of blood leakage from a wound, in particular a wound caused by a cannula or needle or a fistula catheter for arterial or venous punctuation, including punctuation of an AV fistula or graft.

Another object of the present invention is to provide a device of this kind which can be disposed of after single use and which can be economically manufactured.

Further objects of the present invention will become obvious from the following summary of the invention, the description of preferred embodiments thereof illustrated in a drawing, and the appended claims.

SUMMARY OF THE INVENTION

The present invention is based on the insight that it is advantageous from a safety standpoint to dispose a blood detection probe above the wound of a patient rather than laterally of it. A blood detection probe of the invention is one in which an optical or electrical signal changes or arises through the contact of the probe with blood. The head of the probe is the portion of the probe in which the signal or change of signal arises.

In this application the term "cannula" does comprise an AV catheter; insertion of a cannula into an artery or a vein does comprise its insertion into an AV fistula or graft.

This problem is solved according to the invention by a blood leakage detection device for attachment to the skin of a patient at a wound, in particular a wound caused by insertion a cannula into a vein or artery, the device comprising a support of a flexible material, an adhesive zone extending along the periphery of the support except for a sector of from about 5° to about 150°, a blood absorbent patch having a top side and a bottom side disposed on the support and extending inwardly of the adhesive zone and, optionally, in the sector, and a blood detection probe comprising a head disposed at or near the centre of the support in the absorbent patch or, preferably, abutting the absorbent patch at its bottom side, the blood detection probe being selected from the group consisting of: pair of electrodes, radio antenna means, bend or discontinuity of an optical fibre, in particular an optical fibre comprising a sharp bend, piezoelectric element. Most preferred is an optical fibre probe with a probe head comprising or consisting of a sharp bend, in particular a bend of about 180° from a straight state. At its free ends the optical fibre has connectors to put it in radiative communication with electronic light emission and detection means in a blood leakage detection apparatus of known kind, such as the apparatus disclosed in WO 2006/001759. From the foregoing it is to be understood that the probe head is disposed in the device in a manner that it can be disposed over a wound and that blood from the wound can travel to the probe in a direction perpendicular to the skin that surrounds the wound. It is also to be understood from the foregoing that a zone lacking adhesive for attachment to the skin extends from the probe to the periphery of the device. The zone lacking adhesive is intended to be disposed over the cannula when applying the device to the patient's skin around the wound. This disposition will protect the device from adhering to the cannula and thus from being removed with the cannula in the event that the cannula is accidentally withdrawn from the wound. The accidental removal of the device has to be avoided by all means since it might result in a serious blood leakage not being detected. It is preferred for the fibre arms extending from the probe head to be disposed in a radial direction opposite of that of the adhesive lacking sector. According to a preferred variation the blood detection probe comprises an optical fibre comprising a probe head having a discontinuity such as a narrowed or widened section which, when contacted by blood, attenuates light conducted by the fibre.

If not otherwise determined, in this application the indication of a direction in a plane parallel of the skin to which the device is applied is based on that of the optical fibre or the generally parallel arms of the fibre. A direction along the fibre towards its bend is termed frontal. An area facing in that direction is a front face. The opposite direction is a rearward direction. A rear face faces in that direction. "Inner" relates to the inside of the optical fibre bend. In a direction perpendicular to such plane "top" indicates a greater distance from the skin or an element of the device intended for abutment to the skin than "bottom".

According to a first preferred aspect of the invention the support is U-formed, comprising a base and two legs extending from the base. It is preferred for the adhesive for attachment to the skin on one face of the support to extend along its outer periphery but not along its inner periphery.

The support may be provided in two parts, one integrated with the device and lacking adhesive, the other separate of the device and provided with adhesive on its bottom side and being attachable to the part integrated with the device at the periphery thereof so as to thereby make the device attachable to the skin around a wound above which the device is to be disposed; this separate part may be of medical adhesive tape of suitable form adapted to the form of the device which it should overlap when applied, for instance of horseshoe-like form. It is preferred for the support to be substantially impenetrable to blood.

According to a second preferred aspect of the invention the device comprises a blood transport element or layer disposed between the support and the absorbent patch. The transport element or layer is preferably of a material that does not absorb blood. Moreover, it is preferred for the transport element or layer to have a net-like structure. It is also preferred for the transport element to consist of a synthetic polymer material that is impenetrable to blood or to be entirely covered by such material. While blood may adhere to the transport element, the adhering blood does not comprise more than 5 per cent, more preferred more than 2 per cent, of the amount of blood that the absorbent patch can absorb.

According to a third preferred aspect of the invention the probe head is in abutment with top side of the blood transport element.

According to a fourth preferred aspect of the invention the support and the transport element are integral.

According to a fifth preferred aspect of the invention the device comprises a cover attached to the top side of the support, that is, the side of the support opposite to the side that carries adhesive for attachment to the skin, the cover comprising or consisting of a flexible polymer material. It is preferred for the periphery of the cover to coincide, preferably at least over an angle of 210°, with the periphery of the support. Preferably the cover comprises a material and/or an opening allowing fluid to escape from the absorbent patch.

The invention will now be explained in greater detail by reference to a number of preferred embodiments illustrated in the figures of a drawing.

DESCRIPTION OF THE FIGURES

FIG. 3 is a sectional view A-A of the embodiment of FIG. 1 in a state prior to use;

FIG. 4 is the embodiment of FIG. 1 in the state of FIG. 2, in the same view as in FIG. 3;

FIG. 5 is a second embodiment of the disposable blood leakage detection device of the invention, in the same view as that of FIG. 2;

FIGS. 5a and 5b are enlarged sectional views B-B and C-C of an optical fibre holder of the embodiment of FIG. 5;

DESCRIPTION OF PREFERRED EMBODIMENTS

Figure 1:
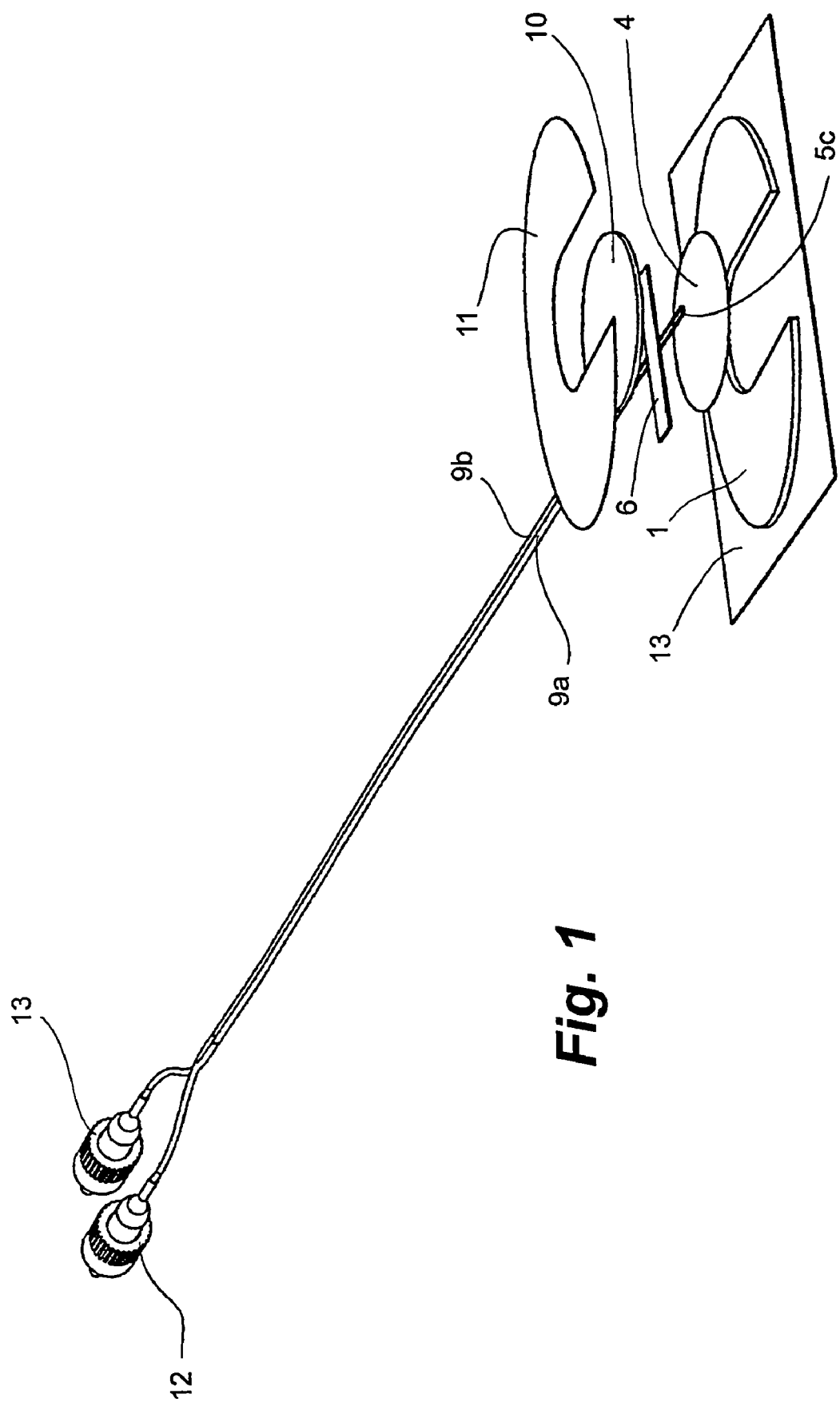
FIG. 1 is a first embodiment of the disposable blood leakage detection device, in an exploded view.
Figure 2:
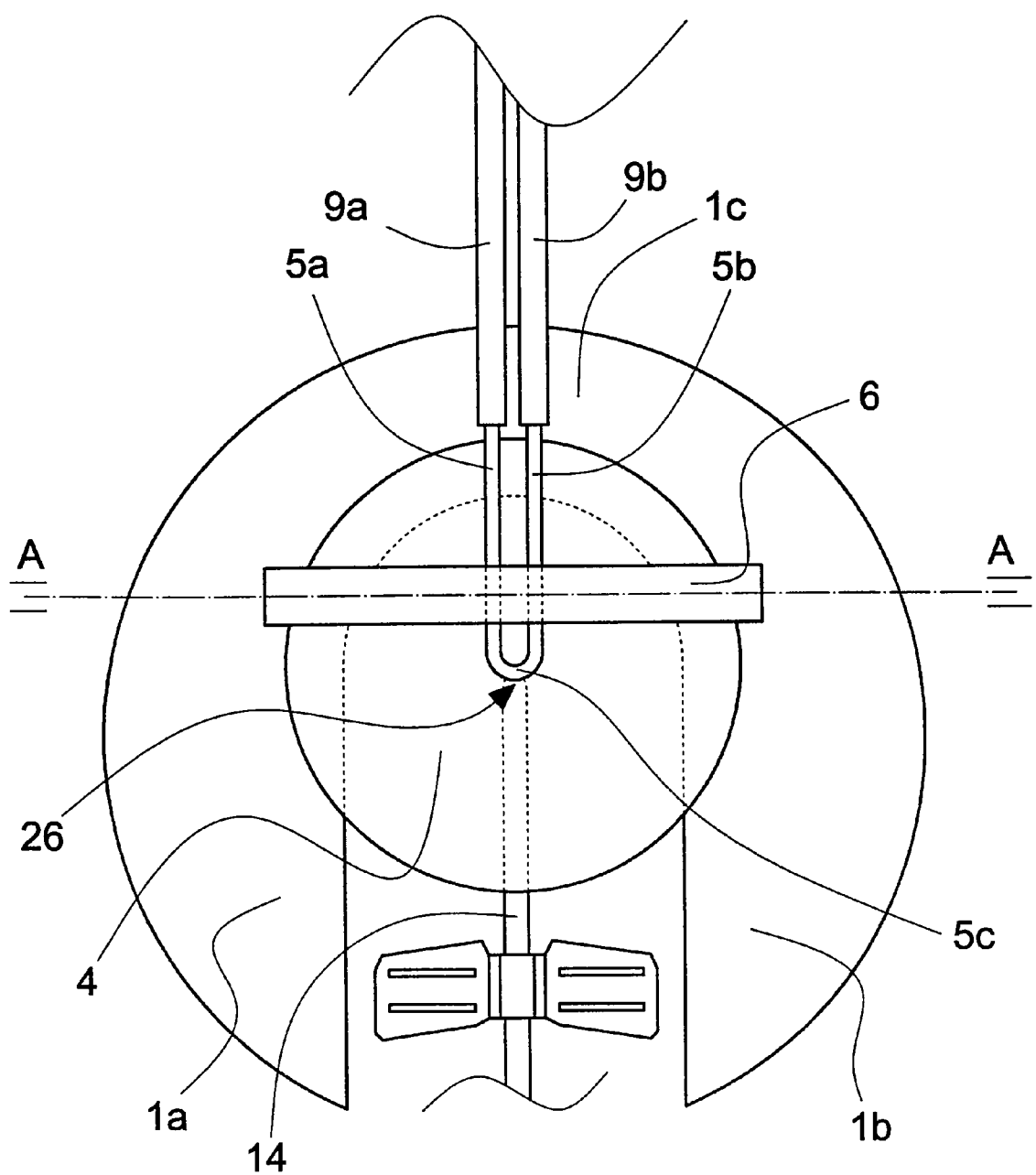
FIG. 2 is a top view of the device in FIG. 1 shown in a state applied to the skin of a patient over a cannula inserted into a vein, with the absorbent patch and the cover removed.

A first embodiment of the disposable blood leakage device of the invention of FIGS. 1-4 comprises a U-formed polyester support 1 consisting of a base 1a and two legs 1b, 1c. The support 1 is essentially impervious to blood. The support 1 is coated with acrylate adhesive on its both sides so as to form a first adhesive layer 2 intended to be applied to the skin of a patient and a second adhesive layer 3 on its opposite face. The adhesive layer 2 facing the skin 20 is protected by a removable silicone coated paper liner 4. A suitable material for the thus coated and protected support 1 is marketed by the 3M Company, U.S.A under the product name 3M™ Double Coated Spunlace Nonwoven Tape 9917. A blood passage element 4 is disposed on the second adhesive layer 3 of the support 1. The blood passage element 4 bridges a portion of the interstice between the legs 1b, 1c of the support 1 extending from the base 1a, and extends as well of inner portions of the legs 1b, 1c and of the base 1a. The blood passage element 4 has the form of a thin circular net. A suitable material for the blood passage element 4 is Delnet X530, which is a net of high density polyethylene (HDPE) homopolymer (Delstar Inc., Bristol, UK). A sharp 180° bend 5c of a blood detection optical fibre 5a, 5b, 5c is disposed centrally on the blood passage element 4 and held there by a piece of rectangular non-woven polyester tape 6, end portions of which extend outside of the circumference of the blood passage element 4 and over the support 1. The optical fibre 5a, 5b, 5c is suitably one of a polymer material, such as poly(methyl methacrylate) (PMMA), of a diameter of about 0.25 mm. In this embodiment the bend 5c is a permanent accomplished by warming a portion of a straight fibre to a temperature at which the polymer material starts to soften, bending the fibre as desired, and cooling it to a temperature below the softening temperature while keeping it in the bent state. On its face abutting the optical fibre arms 5a, 5b and the support 1 the non-woven tape 6 is provided with a hot-melt adhesive 7 that can be cured at a temperature above 40° C. and thereby fixed the optical fibre arms 5a, 5b, the passage element 4, and the support 1. The arms 5a, 5b of the optical fibre 5 extending from the bend 5a run in a direction so as to cross the base 1a of the support 1 about centrally. Except for short portions joining the bend 5c the arms 5a, 5b are covered by shrinking polymer tubes 9a, 9b, respectively. The free ends of the arms 5a, 5b are provided with contacts 12, 13 by which they can be brought into optical contact with a radiation source and a radiation detector, respectively, of a control unit provided with alarm means, such as the one described in WO 2006/001759 A1. A circular non-woven absorbent patch 10 is disposed congruently on the blood passage element 4 so as to enclose the bend 5a of the optical fibre 5 between it and the blood passage element 4. A suitable material for the absorbent patch 10 is the rayon-based 3M™ Medical Absorbent Nonvwoven 1603 comprising a non-adherent polyethylene backing 8 on its one side; the side with the backing is mounted so as to face away from support 1. The absorbent patch 10 is held in place by a cover 11 of a polymer film of which one face is provided with an adhesive 12. A suitable material is 3M Single Coated Polyethylene Medical Tape 1521. The cover 11 corresponds in form to the support 1 and is disposed congruently on top of it to make its adhesive coat 12 abut the adhesive layer 2 of the support 1 and become laminated to it. Prior to application of the device to the skin of a patient the protective liner 13 is removed. The device of the invention is attached by means of the adhesive layer 2 to an area of the skin 20 adjacent to the point of insertion 26 of a cannula 14 through the skin 20 and tissue 21 beneath the skin 20 into a vein 22 to adduce or remove blood to or from the lumen 23 of the vein 22 via the lumen 15 of the cannula 14. The real-life performance of this embodiment investigated in a venous punctuation test, in which the cannula 14 was removed intentionally and the time between removal and alarm was recorded. It was found that the reaction time (the time period from removal to alarm) was from 1 to 3 seconds, where the reaction time of a corresponding embodiment in which the non-absorbing netted blood passage element 4 had been exchanged for a patch of same material as the absorbent patch 10 was generally 3 seconds or longer. Similarly, comparison of this embodiment of the present invention with the disposable blood leakage detection device of WO 2006/001759 A1 demonstrated a superior performance of the former in terms of reaction time length and repeatability.

The second embodiment of the disposable blood leakage device of the invention of FIGS. 5, 5a, 5b differs from the first embodiment by the 105c of the optical fibre 105a, 105b, 105c being accomplished by a fibre holder 130 of a polymer material, such as polystyrene. The symmetric fibre holder 130 comprises two generally flat wings 135, 136 extending from opposite sides of a central portion 137, which comprises a fibre insertion limiting flanges 133a, 133b, a fibre withdrawal limiting finger 134 and bend formation clamping flanges 131a, 131b. The fibre 105a, 105b, 105c is mounted on the fibre holder by forming a temporary bend and inserting the fibre with the temporary bend foremost into a channel 138 in a central guide element 132 until stopped by rear faces of flanges 133a, 133b abutting frontal end faces of polyvinylchloride shielding tubes 109a 199b on the fibre arms 105a, 105b, respectively. Front portions of the arms 105a, 105b adjacent to the bend 105c pressed into slits formed between slightly flexible clamping flanges 131a, 131b and the withdrawal limiting finger 134 and held there by the flanges. The blunt front end of the withdrawal limiting 134 then abuts inside of the bend 105c. It is to be understood that the distance between the bend 105c and the frontal end faces of the shielding tubes 109a, 109b has to match the distance between the front end of the withdrawal limiting finger 134 and the rear faces of flanges 133a, 133b. This can be accomplished by removing appropriate portions of the shielding tubes 133a, 133b. The fibre holder with the mounted fibre 105a, 105b, 105c is mounted between a blood passage element 104 corresponding to element 4 of the first embodiment and an absorbent patch (not shown) corresponding to the patch 10 of the first embodiment, and held in this position by a cover (not shown) corresponding to the cover 11 of the first embodiment. In a state of the device mounted to the skin of a patient the bend 105c is disposed above the skin insertion point of a venous cannula 114.

Figure 6:
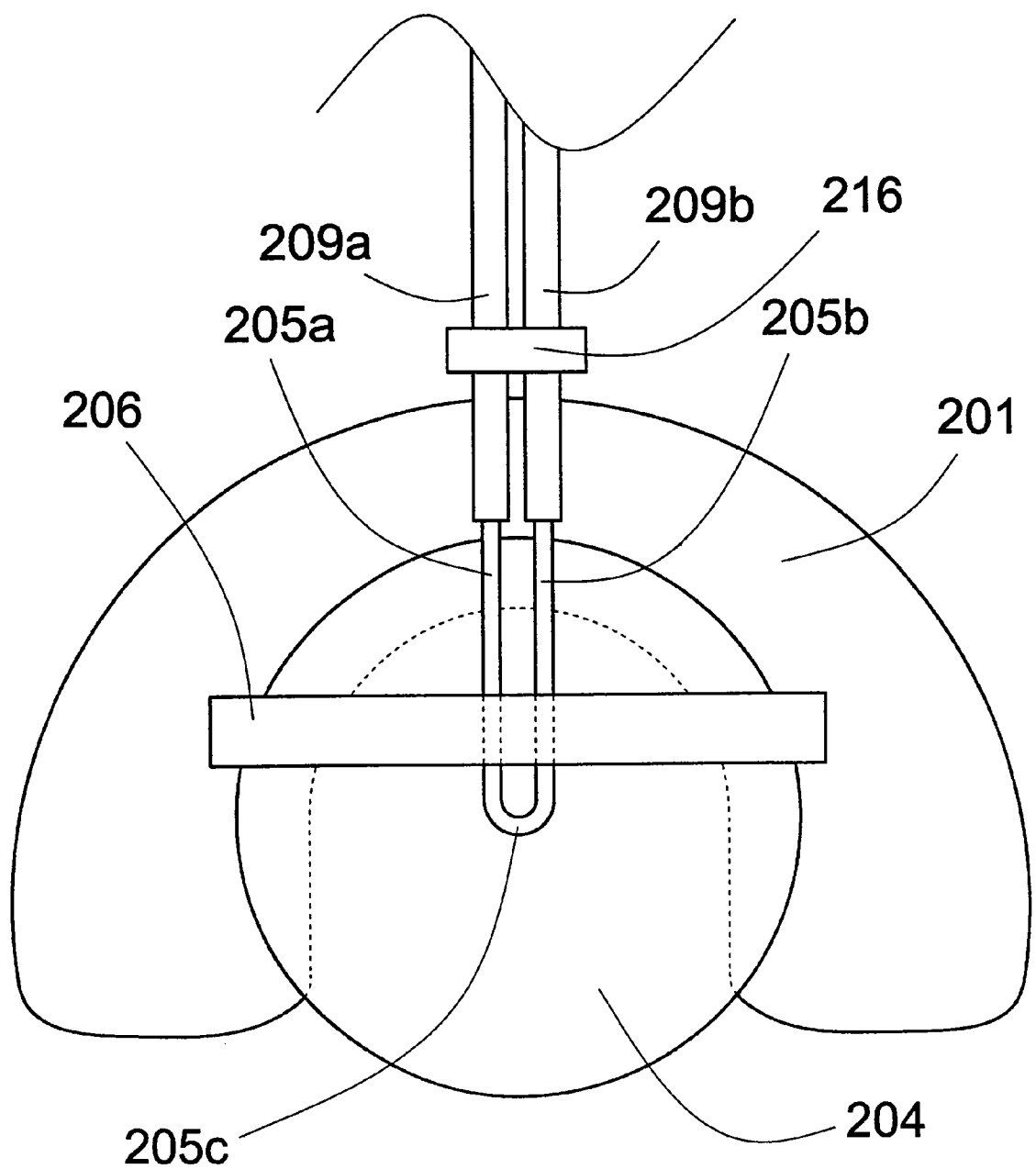
FIG. 6 is a third embodiment of the disposable blood leakage detection device of the invention, in the same view as that of FIG. 2 but with the cannula not shown.

The third embodiment of the disposable blood leakage device of the invention of FIG. 6 differs from the first embodiment by a difference in form of the support 201 and the cover (not shown) of corresponding shape. The arms 205a, 205b of the optical fibre are held in a parallel relationship by girds attached to the shielding tubes 209a, 209b, of which one one gird 216 is shown. The permanent fibre bend 205c is kept attached to a passage element 204 corresponding to passage elements 4 and 114 of the first and second embodiments, respectively. An absorbent patch (not shown) corresponding to the patches 10 and 110, respectively of the first embodiment, is held in this position by a cover (not shown) corresponding to the covers 11 and 111 of the first and second embodiments, respectively.

Figure 7:
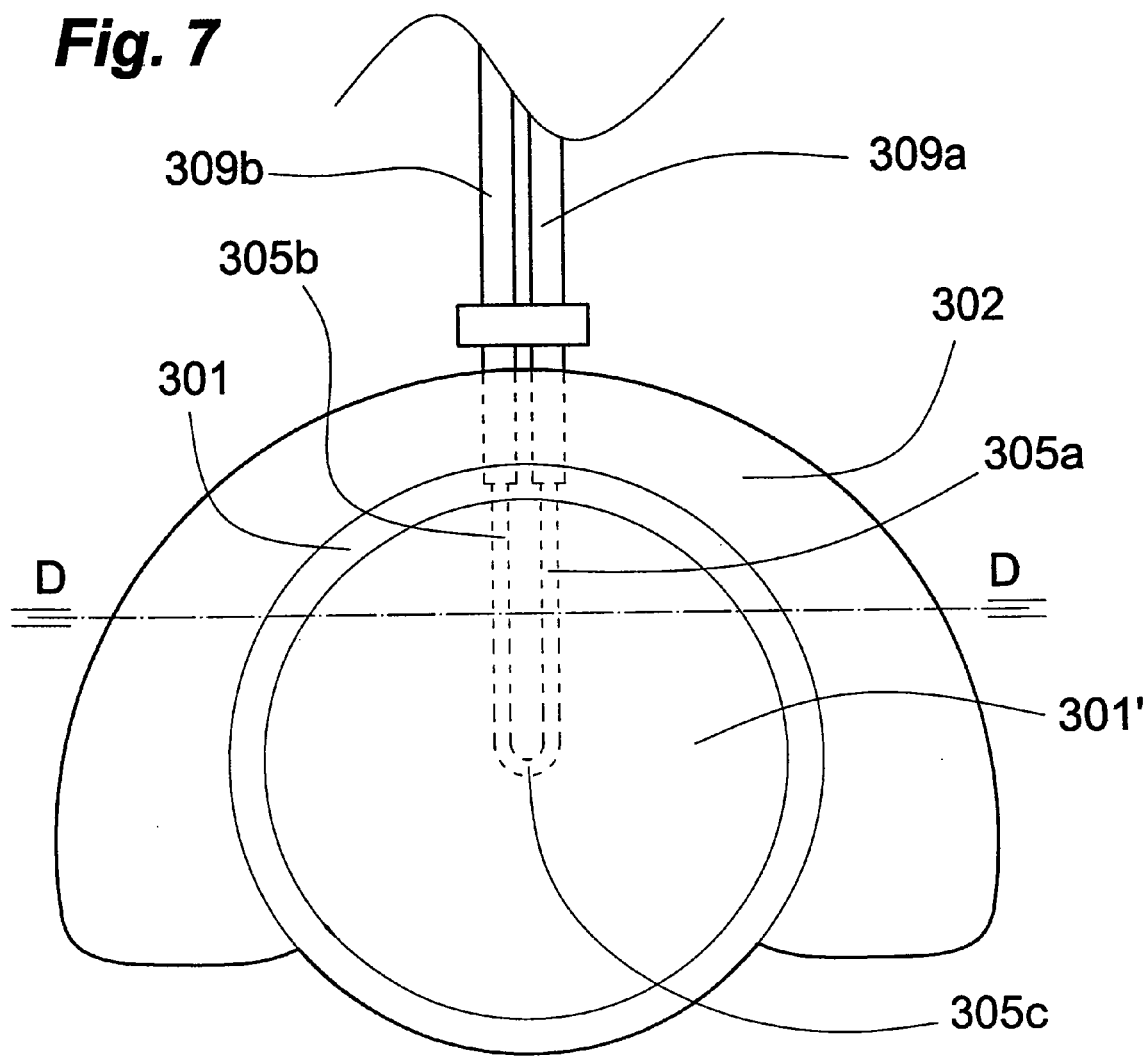
FIG. 7 is a fourth embodiment of the disposable blood leakage detection device of the invention, in a bottom view but lacking the adhesive protection liner.
Figure 8:
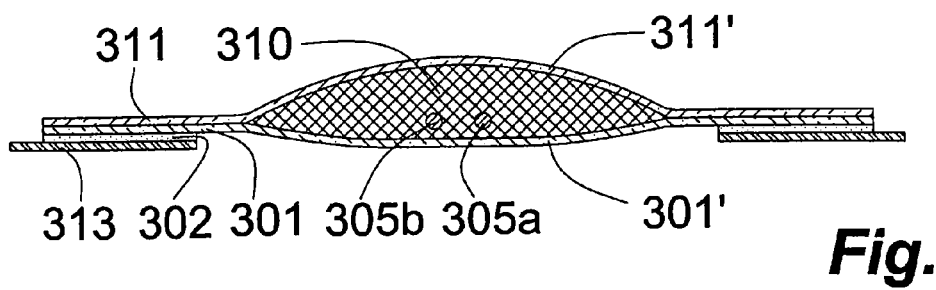
FIG. 8 is a section D-D through the embodiment of FIG. 7, with the siliconized adhesive protection liner also shown.

In the fourth embodiment of the disposable blood leakage device of the invention of FIGS. 7 and 8 the support and the passage element are integrated into one element 301, 301', which retains blood passage capability except for a peripheral U-formed zone covered with acrylate adhesive 302. A front end portion of the optical fibre 305a, 305b, 305c is disposed in an absorbent patch 310, which is held between the central, non-laminated portion of the 301' of the support and passage element 301, 301' and a central, non-laminated portion 311 of a cover 311, 311' congruent in form with the support and passage element 301, 301'. A U-formed peripheral zone of the laminated portion 311 of the support and passage element 311, 311' is covered with acrylate adhesive 312 for attachment to the skin of a patient. For transport and storage it is protected by a thin siliconized paper liner 313, which can be easily torn off. The support and passage element 301, 301' can be laminated to the cover 311, 311' by heat or by means of an s adhesive (not shown). Instead of or in addition to permitting easy passage of air through it the cover may comprise a central opening, in particular one of a circular shape.

Figure 9:
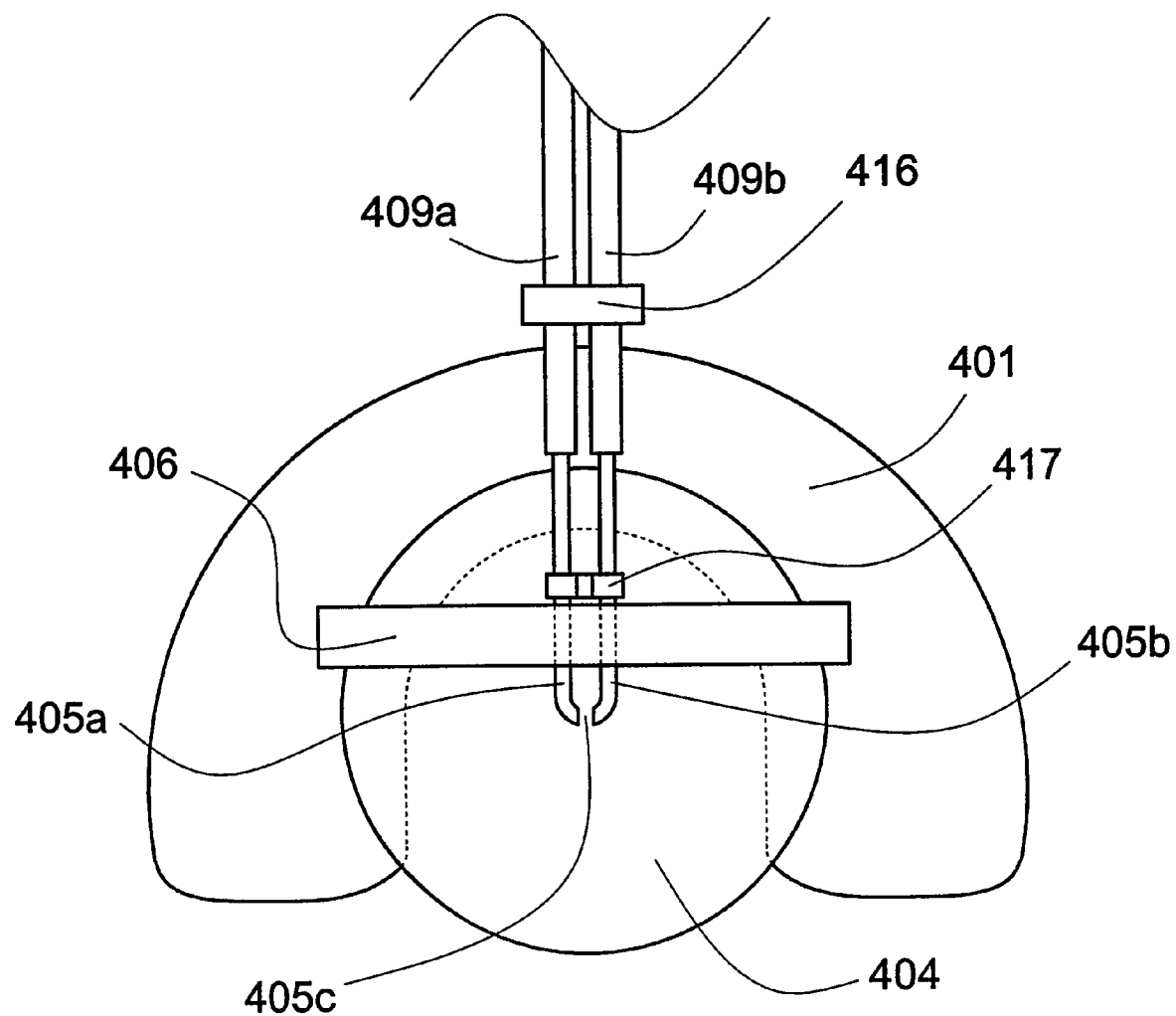
FIG. 9 is a fifth embodiment of the disposable blood leakage detection device of the invention, in a view corresponding to that of FIG. 6.

In the fifth embodiment of the disposable blood leakage device invention of FIG. 9 the detection of a leakage of blood is by a change in electrical conductance in a circuit comprising two metal wires 405a, 405b separated by a slit 405c. At their other free ends the wires 405a, 405b are connected to the poles of a low voltage electrical battery, one of them via a current detection means. The battery and the ampere meter are disposed in a monitoring unit (not shown). The monitoring unit can be, for instance, attached to the arm of the patient on which the device is disposed over a wound such as one caused by a hypodermic needle. Starting at a short distance from the slit 405c the wires are insulated (409a, 409b). The width of the slit 405c is controlled by a spacer 417 of polypropene keeping the naked wires 405a, 405b apart. A second spacer 416 holding the insulated portions 409a, 409b of the wires 405a, 405b is disposed externally of the device. The device of FIG. 9 corresponds to that of FIG. 6, except for the conductance probe head, that is, the slit 405c and the front end portions of the wires 405a, 405b having been substituted for the optical fibre probe head. A leakage of blood is detected by the blood entering the slit 405 thereby establishing electrical connection between the wires 405a, 405b. The resulting current in the circuit is detected by current detection means such as ampere meter, which can be coupled to an alarm means. To provide for good wetting the facing ends of the wires 405a, 405b should be cleaned to remove oil and dirt. A narrow slit will enhance wetting by the capillary effect.

The invention claimed is:

1. Blood leakage detection device for attachment to the skin of a patient at a wound, in particular a wound caused by insertion a cannula into a vein or artery, the device comprising a support of a flexible material having a top side and a bottom side, a zone of adhesive for attachment to the skin on the bottom side of the support extending along its periphery except for a sector of from about 5° to about 150°, a blood absorbent patch having a top side and a bottom side disposed on the support and extending inwardly of the adhesive zone and, in the sector, and a blood detection probe comprising an optical fibre for disposition above the wound, the probe comprising a probe head for disposition above the wound, the probe head being disposed at or near the centre of the support in the absorbent patch or in abutment with the bottom side of the absorbent patch, and inward of the adhesive zone.

2. The device of claim 1, wherein the optical fibre comprises a bend or discontinuity.

3. The device of claim 2, wherein the probe head comprises a discontinuity which, when contacted by blood, attenuates light conducted by the fibre.

4. The device of claim 1, wherein the support is U-formed and the probe head is disposed between the legs of the U.

5. The device of claim 4, wherein the adhesive for attachment to the skin on one face of the support extends along its outer periphery but not along its inner periphery.

6. The device of claim 1, wherein the support is substantially impenetrable to blood.

7. The device of claim 1 comprising a blood transport element or layer of a material that does not absorb blood, disposed between the support and the absorbent patch.

8. The device of claim 7, wherein the transport element or layer has a net-like structure.

9. The device of claim 7, wherein the blood-adhering capacity of the transport element is 5 percent or less of the blood-absorbing capacity of the absorbent patch.

10. The device of claim 7, wherein the transport element is in abutment with the probe head.

11. The device of claim 7, wherein the support and the transport element are integral.

12. The device of claim 1 comprising a cover attached to the top side of the support, the cover comprising a flexible polymer material.

13. The device of claim 12, wherein the periphery of the cover coincides over an angle of at least 210° with the periphery of the support.

14. The device of claim 12, wherein the cover comprises a material and/or an opening allowing fluid to escape from the absorbent patch.

15. The device of claim 1, wherein the support consists of two parts, one integrated with the device and lacking adhesive, the other separate of the device and provided with adhesive on its bottom side and being attachable to the part integrated with the device at the periphery thereof so as to thereby make the device attachable to the skin.

16. The device of claim 15, wherein the part of the support separate of the device is of medical adhesive tape.

17. The device of claim 1, wherein the support is substantially impenetrable to blood.

18. The device of claim 1, wherein the optical fibre comprises a sharp bend.

19. The device of claim 18, wherein the sharp bend is a bend of about 180°.

* * * * *